United States Patent
Valentin et al.

(10) Patent No.: US 12,396,715 B2
(45) Date of Patent: Aug. 26, 2025

(54) TENSIONABLE KNOTLESS ANCHORS AND METHODS OF TISSUE REPAIR

(71) Applicant: Arthrex, Inc., Naples, FL (US)

(72) Inventors: Jason A. Valentin, Fort Myers, FL (US); Nathanael I. Gamso, Cape Coral, FL (US)

(73) Assignee: Arthrex, Inc., Naples, FL (US)

( * ) Notice: Subject to any disclaimer, the term of this patent is extended or adjusted under 35 U.S.C. 154(b) by 524 days.

(21) Appl. No.: 17/709,840

(22) Filed: Mar. 31, 2022

(65) Prior Publication Data

US 2023/0309984 A1 Oct. 5, 2023

(51) Int. Cl.
*A61B 17/04* (2006.01)
*A61B 17/06* (2006.01)

(52) U.S. Cl.
CPC ...... *A61B 17/0401* (2013.01); *A61B 17/0485* (2013.01); *A61B 17/06166* (2013.01); *A61B 2017/0409* (2013.01); *A61B 2017/0414* (2013.01); *A61B 2017/0464* (2013.01); *A61B 2017/0496* (2013.01); *A61B 2017/06185* (2013.01)

(58) Field of Classification Search
CPC ............ A61B 17/0401; A61B 17/0485; A61B 17/0466; A61B 17/06166; A61B 2017/0406; A61B 2017/0409; A61B 2017/0414; A61B 2017/0417; A61B 2017/0464; A61B 2017/0477; A61B 2017/0496; A61B 2017/06185; A61B 2017/00526; A61B 2017/0458; A61B 2017/0445; A61F 2/08; A61F 2/0811
See application file for complete search history.

(56) References Cited

U.S. PATENT DOCUMENTS

| | | | |
|---|---|---|---|
| 8,608,777 B2 | 12/2013 | Kaiser et al. | |
| 8,672,968 B2 | 3/2014 | Stone et al. | |
| 8,986,346 B2 | 3/2015 | Dreyfuss | |
| 9,060,763 B2 | 6/2015 | Sengun | |
| 9,486,202 B2 | 11/2016 | Ferguson | |
| 9,486,204 B1 * | 11/2016 | Ferguson | A61F 2/0811 |

(Continued)

FOREIGN PATENT DOCUMENTS

| | | | |
|---|---|---|---|
| EP | 2698128 B1 | 7/2017 | |
| WO | WO-2020256853 A1 * | 12/2020 | ....... A61B 17/00234 |
| WO | WO-2021155148 A1 * | 8/2021 | ......... A61B 17/0401 |

OTHER PUBLICATIONS

Invitation to pay additional fees for International Application No. PCT/US2023/010737 dated Mar. 29, 2023.

(Continued)

*Primary Examiner* — Ryan J. Severson
(74) *Attorney, Agent, or Firm* — Potomac Law Group, PLLC

(57) ABSTRACT

Tensionable, knotless, self-locking surgical constructs and methods for surgical repairs are disclosed. A soft suture anchor and a flexible strand (flexible coupler) are provided integrally, as a one-piece machine taper construct. The repair system can include one or more shuttle/pull devices. The suture comes out of the cannulated sheath and braids to a smaller diameter round suture which is then passed back through the sheath. The braided suture may be furcated or branched to provide a plurality of passing sutures.

6 Claims, 6 Drawing Sheets

(56) References Cited

U.S. PATENT DOCUMENTS

| | | | |
|---|---|---|---|
| 9,486,211 B2 | 11/2016 | Stone et al. | |
| 9,498,204 B2 | 11/2016 | Denham et al. | |
| 9,572,655 B2 | 2/2017 | Denham et al. | |
| 9,801,708 B2 | 10/2017 | Denham et al. | |
| 9,833,230 B2 | 12/2017 | Stone | |
| 10,004,493 B2 | 6/2018 | Stone et al. | |
| 10,070,856 B1* | 9/2018 | Black | A61B 17/0401 |
| 10,092,288 B2 | 10/2018 | Denham et al. | |
| 10,136,886 B2 | 11/2018 | Norton et al. | |
| 10,265,060 B2 | 4/2019 | Dooney et al. | |
| 10,327,755 B2 | 6/2019 | Feezor et al. | |
| 10,335,136 B2 | 7/2019 | Dooney et al. | |
| 10,349,931 B2 | 7/2019 | Stone | |
| 10,398,428 B2 | 9/2019 | Denham et al. | |
| 10,517,587 B2 | 12/2019 | Denham et al. | |
| 2013/0110165 A1 | 5/2013 | Burkhart et al. | |
| 2013/0296931 A1 | 11/2013 | Sengun | |
| 2013/0296934 A1* | 11/2013 | Sengun | A61B 17/06166 606/232 |
| 2014/0052179 A1 | 2/2014 | Dreyfuss et al. | |
| 2014/0249577 A1 | 9/2014 | Pilgeram | |
| 2014/0257382 A1 | 9/2014 | McCartney | |
| 2015/0173739 A1 | 6/2015 | Rodriguez et al. | |
| 2019/0038276 A1 | 2/2019 | Jackson | |
| 2019/0099258 A1* | 4/2019 | Armington | A61F 2/4202 |
| 2019/0223857 A1 | 7/2019 | Sengun | |
| 2019/0365366 A1 | 12/2019 | Petry et al. | |
| 2020/0187933 A1* | 6/2020 | Kaiser | A61F 2/0811 |
| 2020/0268502 A1* | 8/2020 | Brunsvold | A61F 2/0811 |
| 2021/0244402 A1 | 8/2021 | Leffler | |
| 2021/0275160 A1 | 9/2021 | Snell et al. | |
| 2021/0290217 A1* | 9/2021 | Biedermann | A61B 17/0401 |
| 2021/0353280 A1 | 11/2021 | Black et al. | |
| 2022/0096074 A1* | 3/2022 | Denham | A61F 2/08 |
| 2023/0146316 A1* | 5/2023 | Stone | A61B 17/06166 606/228 |
| 2023/0338017 A1* | 10/2023 | Lund | A61B 17/0401 |

OTHER PUBLICATIONS

International Search Report and Written Opinion for International Application No. PCT/US2023/010737 dated Jun. 23, 2023.
Examination report for Australian Patent Application No. 2023245612 issued on Jun. 12, 2025.

* cited by examiner

TENSIONABLE KNOTLESS ANCHORS AND METHODS OF TISSUE REPAIR

BACKGROUND

The disclosure relates to the field of surgery and, more specifically, to knotless anchor constructs and associated methods of tissue repairs.

SUMMARY

Reconstruction systems, assemblies and methods for fixation of soft tissue are disclosed.

A tensionable, knotless surgical construct can create a knotless, self-locking, reinforced repair. A tensionable, knotless, self-locking surgical construct is made completely of suture(s) to achieve fixation in bone without a separate anchoring body. The design enables fixation by deployment into bone with suture tail(s) remaining outside the bone for tensioning and/or alternative usage. The knotless surgical construct may be employed in knotless fixation of first tissue to second tissue, for example, fixation of tendon to bone.

Methods of tissue repairs are also disclosed. In an embodiment, a knotless surgical construct provides tissue fixation without any knot formation, by providing an all-suture soft anchor device that does not require a separate anchoring body or similar structure.

DETAILED DESCRIPTION

Figure 1:
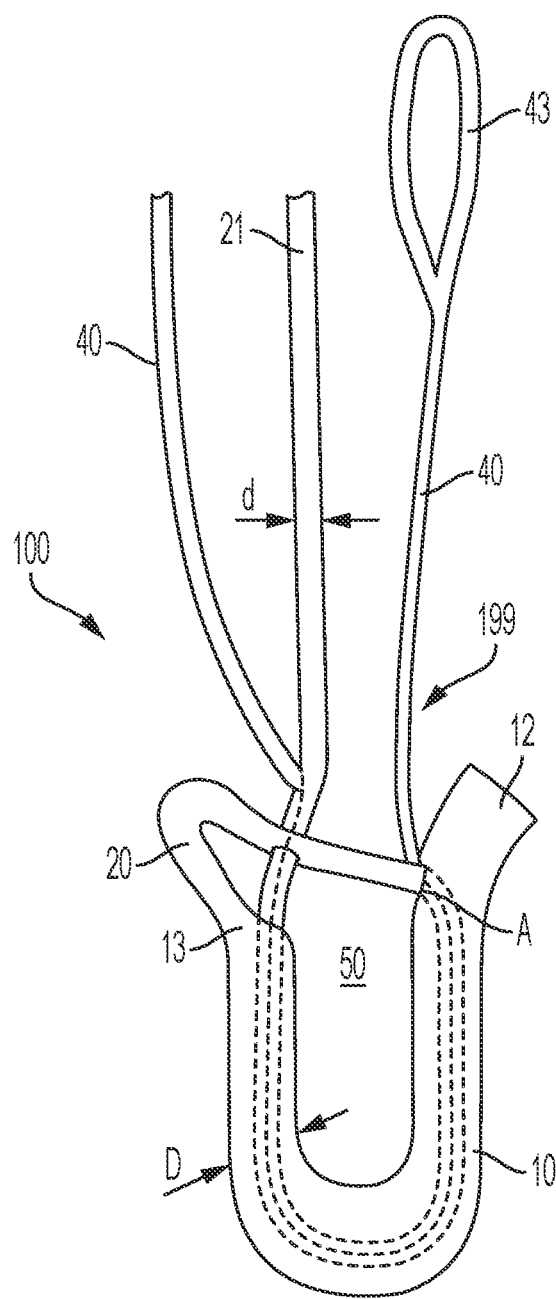
FIGS. 1-5 illustrate schematic views of surgical constructs.

A tensionable, knotless, self-locking surgical construct can create a knotless, reinforced repair.

A soft tissue repair system includes a tensionable, knotless, self-locking surgical construct with a fixation device and a flexible strand (flexible coupler) provided as a one-piece machine taper construct. The repair system can include one or more shuttle/pull devices.

In an embodiment, a soft suture anchor includes a single suture knotless anchor, wherein a soft anchor sheath is provided integral with the repair suture(s) (a "single suture knotless FiberTak® soft anchor"). The suture comes out of the cannulated sheath and braids to a smaller diameter round suture which is then passed back through the sheath. The braided suture may be furcated/branched/forked (for example, bifurcated or trifurcated, etc.) to provide a plurality of passing sutures.

The construct secures tissue (arthroscopic or endoscopic) with a suture that does not require the surgeon to tie a knot. The construct pulls soft tissue together. The furcation(s) in the suture allow the construct to improve tissue cut-through resistance (by reducing the "cheese wire" effect) which is important in many clinical applications. The knotless surgical construct can be employed in knotless fixation of first tissue to second tissue, for example, fixation of soft tissue to bone.

Methods of knotless tissue repairs are also disclosed. In an embodiment, a surgical construct provides knotless first tissue to second tissue fixation, for example, knotless fixation of soft tissue (ligament, tendon, graft, etc.) to bone without any knot formation and in a simple and fast manner.

The sheath and braided suture can be manufactured from any flexible material, for example, multifilament, braided, knitted, woven suture, or including fibers of ultrahigh molecular weight polyethylene (UHMWPE) or the Fiber-Wire® suture (disclosed in U.S. Pat. No. 6,716,234, the disclosure of which is hereby incorporated by reference in its entirety herein). Surgical constructs can be used with any type of flexible material or suture known in the art. The shuttle/pull device can be a suture passing instrument or a shuttle link such as a FiberLink™ or a Nitinol loop.

Referring now to the drawings, where like elements are designated by like reference numerals, FIGS. 1-5 illustrate exemplary surgical construct 100, 200, 300, 400, 100a (implantable device 100, 200, 300, 400, 100a; surgical assembly 100, 200, 300, 400, 100a; surgical system 100, 200, 300, 400, 100a; suture anchor 100, 200, 300, 400, 100a; tensionable, knotless construct 100, 200, 300, 400, 100a; tensionable, knotless, self-locking, surgical anchor 100, 200, 300, 400, 100a) including exemplary fixation device 10 with exemplary knotless, self-locking, tensionable mechanism 199 within a body of the fixation device 10. FIG. 6 illustrates an exemplary soft tissue repair 101 with surgical construct 100.

As detailed below, surgical construct 100, 200, 300, 400, 100a is an implantable device made completely of suture or sutures that achieves fixation in bone without a separate anchoring body. The design enables for fixation by deployment into bone with suture tail or tails remaining outside the bone for tensioning and alternative usage.

Surgical construct 100 of FIG. 1 includes fixation device 10 formed integral (machined integrally) with flexible coupler 20 (flexible strand 20; suture 20; repair suture 20). One or more shuttle/pull devices 40 (suture passing instrument 40; suture passer 40; shuttle link 40; FiberLink™ 40; nitinol loop 40) are provided attached to fixation device 10.

As shown in FIG. 1, fixation device 10 can be in the form of a soft anchor (soft suture anchor, or all-suture soft knotless anchor) provided with a soft anchor sleeve 10 (sheath or tubular member 10) and a cannulation 11 (not shown) with two ends 12, 13. One of the two ends, for example, end 12 is an open end. The other of the two ends, for example, end 13 terminates in, and continues with, flexible coupler 20, i.e., flexible coupler comes out of the cannulated sheath 10 (soft anchor sleeve or sheath) and braids to a smaller diameter strand 20 having a single flexible end 21. In an embodiment, flexible coupler 20 diameter may be the same or smaller suture having a round diameter. In an embodiment, flexible coupler 20 is a single strand of #5 or #2 machine taper suture.

Flexible coupler 20 is passed back through the cannulation 11 of sheath 10 to form at least one flexible, closed, knotless, continuous, adjustable loop 50 having an adjustable perimeter and adjustable length.

FIG. 1 also illustrates one or more shuttle/pull devices 40 extending through the sleeve 10. If more than one shuttle/pull devices 40 are provided, the shuttle/pull devices can extend through the sheath 10 in similar or different directions and/or orientations and/or locations. Details of an exemplary soft suture anchor with a soft anchor sleeve (sheath or tubular member) and flexible shuttling strands are set forth, for example, in U.S. application Ser. No. 15/998,516 entitled "Methods of Tissue Repairs" filed on Aug. 16, 2018 (issued as U.S. Pat. No. 10,849,734 on Dec. 1, 2020), the disclosure of which is incorporated by reference in its entirety herein. The flexible coupler and the one or more shuttle/pull devices can extend through the sleeve in similar or different directions and/or orientations and/or locations.

Flexible coupler 20 is provided with a single terminal end 21. The terminal end 21 is a flexible end (free end 21) that is formed integral with end 13 of the sheath 10. Flexible coupler 20 comes off of the cannulated sheath 10 and is braided to a round suture with a diameter "d" which may be smaller than diameter "D" of the sheath 10. The diameter differentiation and furcation of suture occurs within the manufacturing process (i.e., braiding, weaving, sewing, stitching, etc.). In an embodiment, flexible coupler 20 is a one-piece machine taper construct with sheath 10 and has the form of a round single suture strand of #5 or #2 machine taper suture. The sheath 10 acts as the soft sheath. Shuttle suture 40 (shuttle/pull device 40) is passed through the sheath 10. Shuttle suture 40 (shuttle/pull device 40) is attached to the sheath 10 and/or flexible coupler 20 by being spliced, for example, to the flexible coupler.

As detailed below, end 21 can form one or more flexible, closed, knotless, continuous, adjustable loops 50a, 50b, 50c ... etc. (referred to, for simplicity, as "flexible, closed, knotless, continuous, adjustable loops 50") having an adjustable perimeter and adjustable length.

FIG. 1 illustrates one exemplary shuttle/pull device 40 in the form of a suture passing instrument or a suture passer such as FiberLink™ 40 or nitinol loop 40. However, the disclosure is not limited to this exemplary-only embodiment and contemplates implantable devices provided with a plurality of shuttle/pull devices. If more than one shuttle/pull device 40 is employed, the plurality of shuttle/pull devices can reside within the sheath 10 independent from each other. Suture passing device 40 includes an eyelet/loop 43 for passing the flexible coupler 20. If a plurality of shuttle/pull devices are employed, each of the plurality of shuttle/pull devices can include a corresponding eyelet/loop 43 for passing the flexible coupler 20. The shuttle/pull devices may be similar to each other or different from each other.

The flexible coupler 20 can be passed through at least a portion of the body of the fixation device 10, for example, through a full cannulation of the fixation device, or may enter and/or exit the body of the fixation device at a location other than most distal end and most proximal end of the fixation device, for example, location A in FIG. 1.

As detailed below, either the device is inserted into bone via self-punching driver or, alternatively, subsequent to the insertion of fixation device 10 of surgical construct 100 into a drilled hole in bone 90, the flexible coupler 20 and shuttle/pull device 40 are released from the driver, and the driver removed. Free end 21 of flexible coupler 20 is subsequently passed around or through tissue 80 and then through the eyelet/loop 43 of suture passing device 40. Suture passing device 40 is then pulled, thereby pulling free end 21 of the flexible coupler 20 towards the body of the fixation device, inside of the sheath 10 and then exiting the cannulation 11 of sheath 10 to form another flexible, closed, knotless, continuous, adjustable loop 50. Free end 21 forms a splice inside the sheath 10. The suture end 21 of flexible coupler 20 can then be tensioned and cut.

Figure 2:
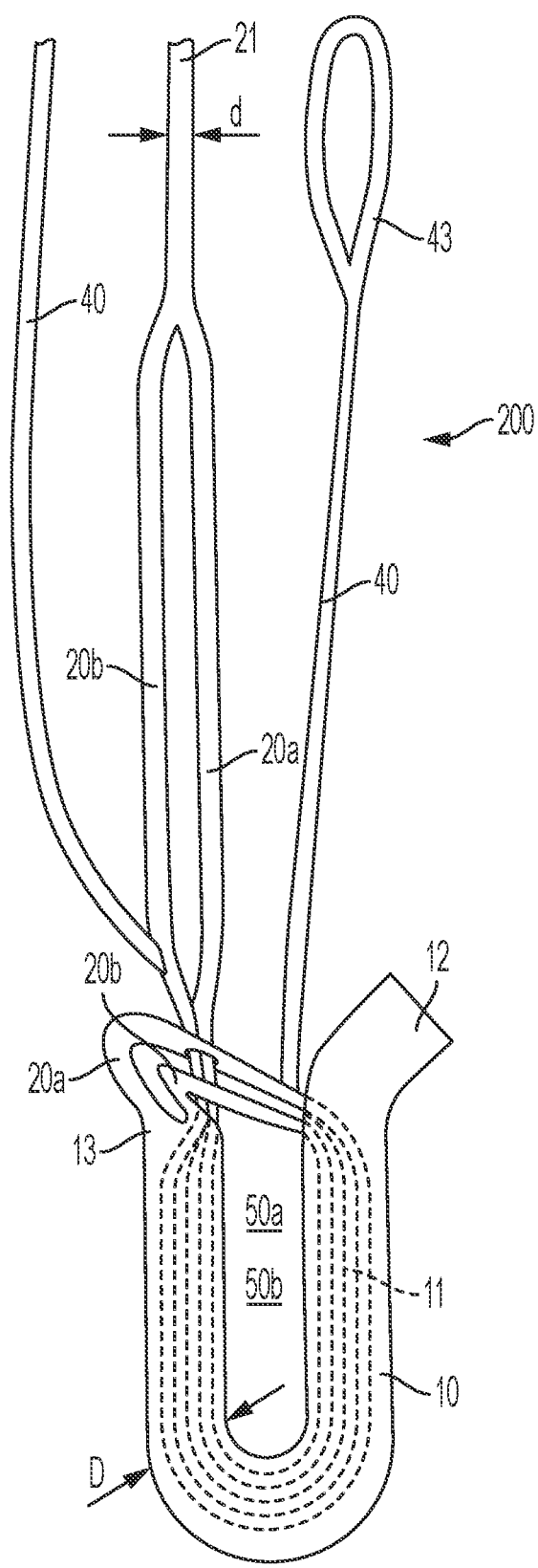
Figure 3:
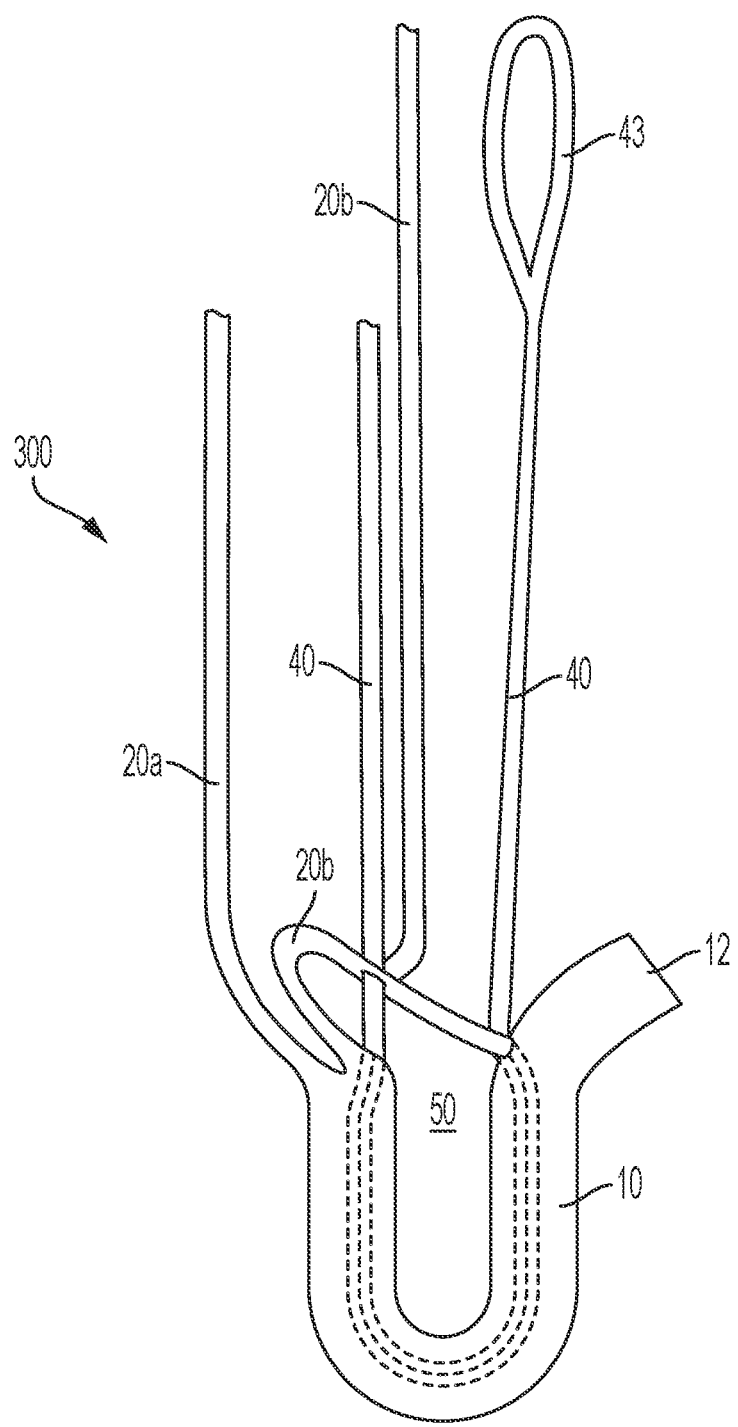
Figure 4:
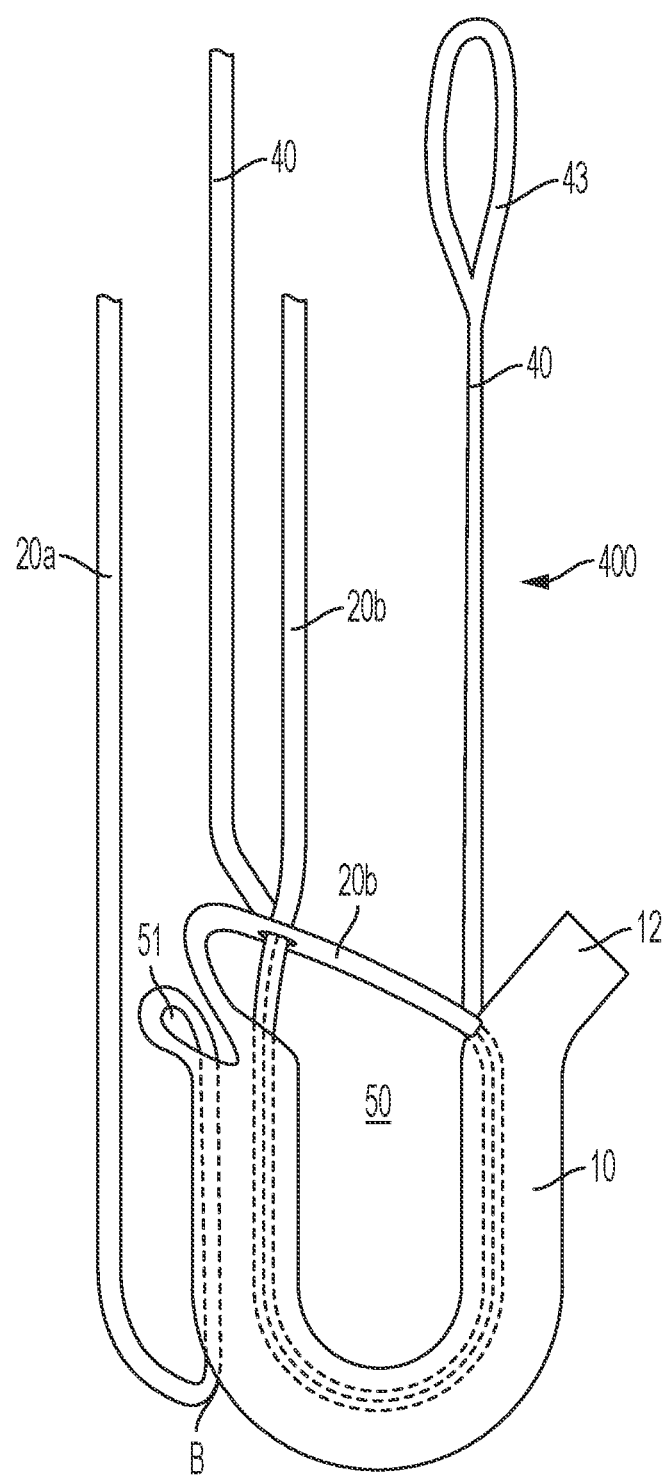

FIGS. 2-4 illustrate soft suture anchors 200, 300, 400 which are about similar to soft suture anchor 100 of FIG. 1 in that they are also one-piece machine taper constructs and they include flexible couplers 20a and 20b provided with a single terminal end 21 that are formed integral with the sheath 10, and shuttle/pull device 40 passed through the sheath 10. However, suture anchor 200 includes flexible couplers 20a and 20b which are bifurcated from the sheath 10 and provide a plurality of loops.

As in the previous embodiment, each of the legs 20a, 20b is passed through the cannulated body of the sheath 10 to form first and second flexible, closed, knotless, continuous, adjustable loops 50a, 50b. Free end 21 of flexible coupler 20 can be subsequently passed around or through the tissue 80 and then through the eyelet/loop 43 of suture passing device 40. Suture passing device 40 is then pulled, thereby pulling free end 21 of the flexible coupler 20 (together with bifurcated legs 20a, 20b) towards the body of the fixation device, inside of the sheath 10 and then exiting the sheath 10 to form additional flexible, closed, knotless, continuous, adjustable loops 50c, 50d (not shown). The suture end 21 of flexible coupler 20 can then be tensioned and cut. Alternatively, with the removal of the suture end 21, the legs 20a, 20b can be set free for formation of additional loops (if additional shuttle/pull devices 40 are provided) or employed for additional surgical steps and as necessary.

FIG. 3 illustrates construct 300 which is also a one-piece machine taper construct with flexible sheath 10 terminating into two suture legs 20a, 20b. One of the two suture legs (for example, suture leg 20b) is passed through the sheath 10 to form flexible, closed, knotless, continuous, adjustable loop 50. Free end 20b can be subsequently passed around and/or through the tissue 80 and then through the eyelet/loop 43 of suture passing device 40. Suture passing device 40 is then pulled, thereby pulling leg 20b towards the body of the fixation device, inside of the sheath 10 and then exiting the sheath 10 to form an additional flexible, closed, knotless, continuous, adjustable loop. Suture leg 20a can be used for other tissue repairs that could include knotted repairs, such as lateral tissue compression with accompanying interference anchors, for example.

FIG. 4 illustrates construct 400 which is also a one-piece machine taper construct with flexible sheath 10 terminating into two suture legs 20a, 20b. One of the two suture legs (for example, suture leg 20b) is passed through the sheath 10 to form flexible, closed, knotless, continuous, adjustable loop 50. The other leg (for example, suture leg 20a) is passed through the sheath 10 and exits at location B to form another loop 51, for additional reinforcement of the construct. Free end 20b can be subsequently passed around or through the tissue 80 and then through the eyelet/loop 43 of suture passing device 40. Suture passing device 40 is then pulled, thereby pulling leg 20b towards the body of the fixation device, inside of the sheath 10 and then exiting the sheath 10 to form an additional flexible, closed, knotless, continuous, adjustable loop. Suture leg 20a can be used for other tissue repairs that can include knotted repairs, lateral tissue compression conducted with accompanying interference anchors, etc.

Figure 5:
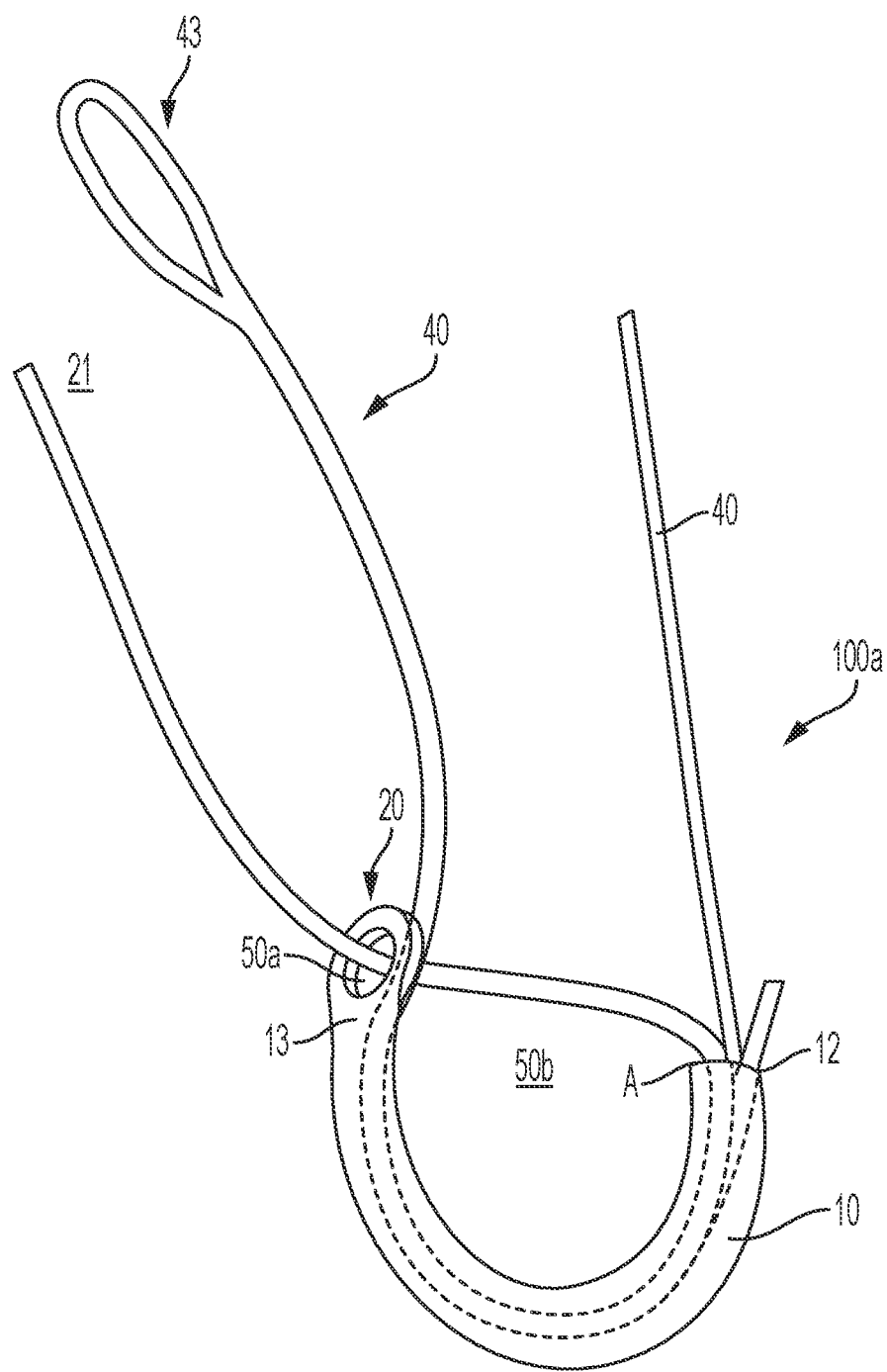
Figure 6:
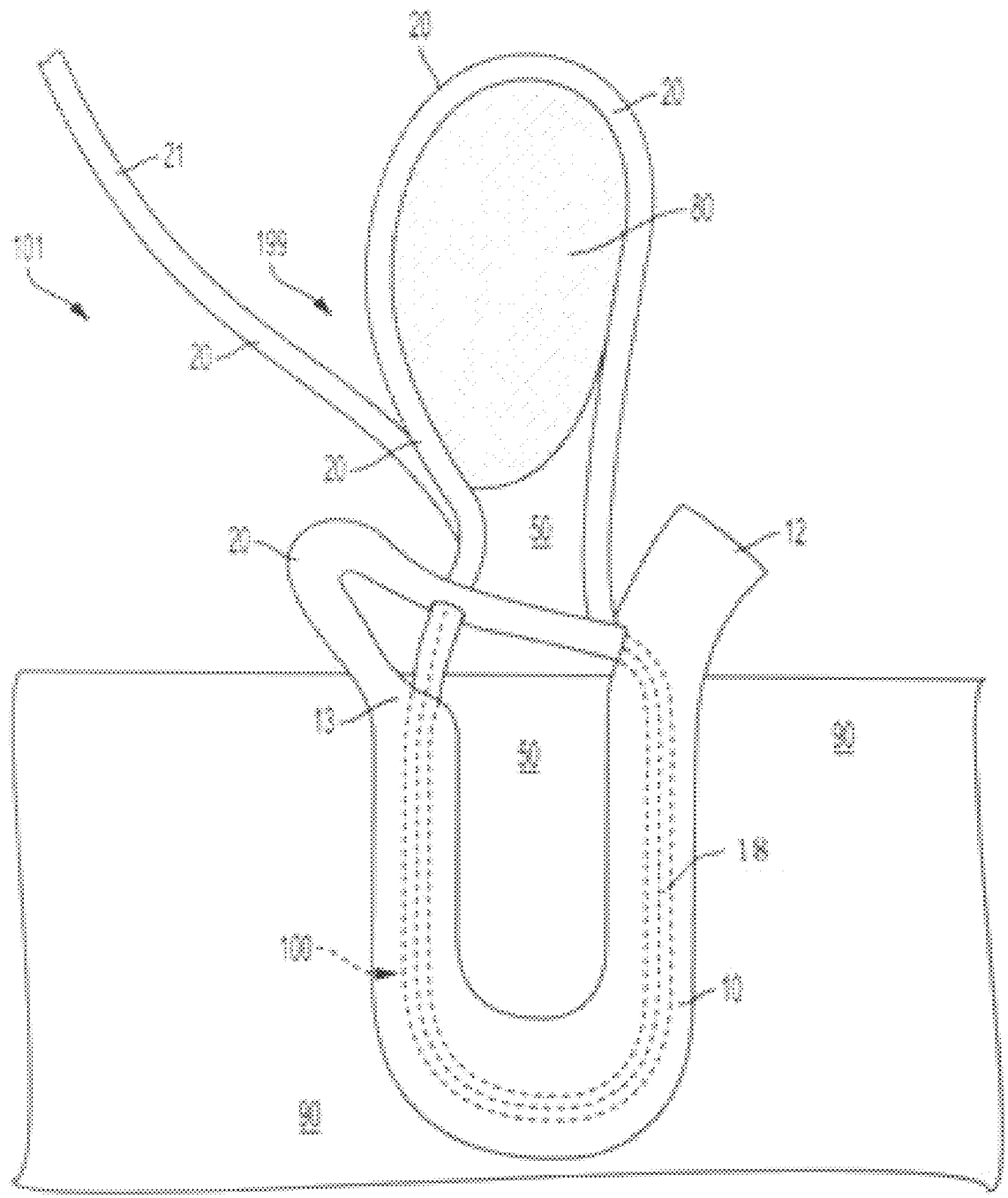
FIG. 6 illustrates a schematic repair with surgical construct of FIG. 1.

FIG. 5 illustrates yet another soft suture anchor 100a which is about similar to soft suture anchor 100 of FIG. 1 in that it is also a one-piece machine taper construct which includes a flexible coupler 20 provided with a single terminal end 21 which is formed integral with the sheath 10, and shuttle/pull device 40 passed through the sheath 10. However, suture anchor 100a differs in how coupler 20 pierces and exits the sheath 10, i.e., it enters the sheath 10 at the same end 13 where it exits to form a first loop or eyelet 50a, passes through the cannulation 11 of the sheath 10, exits at location A at the other end 12, and passes back through first loop 50 to form another loop 50b.

Construct 100a of FIG. 5 is a one-piece machine taper construct sheath 10 that contains a proximal eyelet/loop 50a and exits at location A to form another loop 50b, for additional reinforcement of the construct. Free end 21 can be subsequently passed around or through the tissue 80 and then through the eyelet/loop 43 of suture passing device 40. Suture passing device 40 is then pulled, thereby pulling leg 21 towards the body of the fixation device, inside of the sheath 10 and then exiting the sheath 10 to form an additional flexible, closed, knotless, continuous, adjustable loop. Suture leg 21 can be used for other tissue repairs. Fixation device 10 which can be in the form of a soft anchor (soft suture anchor, or all-suture soft knotless anchor) provided with a soft anchor sleeve 10 (sheath or tubular member 10) and a cannulation 11 (not shown) with two ends 12, 13. One of the two ends, for example, end 12 is an open end. The other of the two ends, for example, end 13 terminates in, and continues with, flexible coupler 20, i.e., flexible coupler comes out of the cannulated sheath 10 (soft anchor sleeve or sheath) and braids to a smaller diameter strand 20 which ends in a single flexible end 21. In an embodiment, flexible coupler 20 may or may not have a smaller diameter suture having a round diameter. In an embodiment, flexible coupler 20 is a single strand suture.

FIG. 6 illustrates a schematic tissue repair 101 (e.g., tendon or ligament repair) with exemplary surgical construct 100 of FIG. 1, to secure a first tissue 80 (for example, soft tissue such as tendon 80) to a second tissue 90 (for example, bone 90). Once flexible sheath 10 of surgical construct 100 has been inserted and secured within a hole in bone 90, the flexible end 21 of flexible coupler 20 is passed around or through tissue 80 and then through eyelet 43 of shuttle/pull device 40. The shuttle/pull device 40 is then pulled out of the fixation device 10 and out of the surgical site, to allow the flexible coupler 20 to pass through the cannulation 11 of sheath 10 (passing through itself and forming a splice 18 within the body of sheath 10) to form a flexible, tensionable, continuous, adjustable, self-locking, cinching, closed loop 50 around tissue 80.

Free end 21 of the flexible coupler 20 can be pulled to shrink the construct and the flexible, closed, knotless, continuous, adjustable loops 50, and to compress the tendon to bone, providing a final repair/construct 101 with increased compression of tissue.

The constructs, systems, and assemblies of the present disclosure may be employed in numerous knotless soft tissue repairs and fixations, for example, fixation of soft tissue to bone.

A soft anchor consists essentially of a flexible tubular member or sheath 10 terminating into a smaller diameter suture 20. The soft anchor is formed as a one-piece machine taper construct. The suture 20 is a round suture. The suture forms at least one splice within the flexible tubular member 10 and at least one adjustable, knotless, closed, continuous loop 50 around a second tissue 80 to be secured to a first tissue 90.

Methods of soft tissue repair which do not require tying of knots and allow adjustment of both the tension of the suture and the location of the tissue with respect to the bone, while providing self-locking mechanism, are disclosed. A method of knotless tissue repair comprises inter alia the steps of: securing a flexible cannulated sheath 10 of a one-piece taper construct 100 into a first tissue 90, the one-piece taper construct 100 being preloaded with a shuttle/pull device 40; and passing a flexible coupler 20 braided out of the sheath 10 around or through a second tissue 80 to be positioned relative to the first tissue 90 and then through the fixation device 10 by employing the shuttle/pull device, to form an adjustable, knotless, closed, continuous loop 50 around the second tissue 80. The knotless, closed, adjustable, flexible, continuous loop 50 can have an adjustable perimeter. The flexible coupler can be passed multiple times through the body of the sheath 10.

As detailed above, when the anchor sheath is inserted, the anchor sheath has at least one repair suture limb (which is fixed to the anchor and manufactured at the same time with the anchor, as a one-piece construct) and also one or more shuttle links. The anchor sheath resides within the bone. The repair suture limb(s) resides on top of the bone. The repair suture is passed around or through the tissue, and then shuttled through the anchor and spliced within the anchor. The steps can be repeated again if additional links are present.

The sheath 10 and braided suture 20 can include any flexible material, for example, multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). FiberWire® suture is formed of an advanced, high-strength fiber material, namely ultrahigh molecular weight polyethylene (UHMWPE), sold under the tradenames Spectra (Honeywell) and Dyneema (DSM) fibers, braided with at least one other fiber, natural or synthetic, to form lengths of suture material.

Flexible coupler 20 can be also formed of a stiff material, or combination of stiff and flexible materials, particularly for the regions of the coupler that are passed/spliced through the body of the coupler and depending on whether they are employed with additional fixation devices. In addition, sheath 10 and flexible coupler 20 can be also coated and/or provided in different colors for easy manipulation during the surgical procedure. The knotless constructs and self-locking soft anchors of the present disclosure can be used with any type of flexible material or suture that may be weaved or passed through itself.

Various structural elements of surgical construct 100, 200, 300, 400, 100a may be visually coded, making identification and handling of the sheath and suture legs simpler. Easy identification of suture in situ is advantageous in surgical procedures, particularly during arthroscopic surgeries, endoscopic and laparoscopic procedures.

The surgical constructs of the present disclosure may be employed in endoscopic surgery. The term "endoscopic surgery" refers to surgical procedures within a patient's body through small openings as opposed to conventional open surgery through large incisions. Additionally, surgical constructs as disclosed herein may be utilized in other general surgical and specialty procedures such as soft tissue repairs.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed:

1. A soft anchor consisting essentially of a flexible tubular member terminating into a smaller diameter suture, wherein the flexible tubular member is configured to be fixated in bone, and wherein the smaller diameter suture passes through itself and through the flexible tubular member at least once and forms at least one splice within the flexible tubular member.

2. The soft anchor of claim 1, wherein the soft anchor is formed as a one-piece machine taper construct.

3. The soft anchor of claim 1, wherein the smaller diameter suture is a round suture.

4. The soft anchor of claim 1, wherein the smaller diameter suture is a #5 or #2 round suture.

5. The soft anchor of claim 1, wherein the smaller diameter suture is configured to form at least one loop around soft tissue to be attached to bone.

6. The soft anchor of claim 1, wherein the smaller diameter suture passes through the flexible tubular member multiple times.

\* \* \* \* \*